United States Patent [19]

Nishibayashi et al.

[11] Patent Number: 5,316,773
[45] Date of Patent: May 31, 1994

[54] PARTICULATE PREPARATION CONTAINING A FLOURRACIL DERIVATIVE AND HYDROXYPROPYLMETHYL-CELLULOSE

[75] Inventors: Toru Nishibayashi; Yoshihiro Ishizue; Kozo Ishida; Masanori Kubo, all of Tokushima, Japan

[73] Assignee: Otsuka Pharmaceutical Co., Ltd., Tokyo, Japan

[21] Appl. No.: 842,195

[22] PCT Filed: Jul. 17, 1991

[86] PCT No.: PCT/JP91/00951
§ 371 Date: Mar. 16, 1992
§ 102(e) Date: Mar. 16, 1992

[87] PCT Pub. No.: WO92/01453
PCT Pub. Date: Feb. 6, 1992

[30] Foreign Application Priority Data
Jul. 19, 1990 [JP] Japan ................... 192112

[51] Int. Cl.$^5$ .................. A61K 9/14; A61K 47/38
[52] U.S. Cl. ................... 424/499; 424/488; 424/487; 424/497; 424/451; 424/456; 424/464
[58] Field of Search ......... 424/486, 487, 497, 488, 424/499, 452, 456, 465, 469–470

[56] References Cited

U.S. PATENT DOCUMENTS

| | | | |
|---|---|---|---|
| 4,127,647 | 11/1978 | Sato et al. | 424/78 |
| 4,343,789 | 8/1982 | Kawata et al. | 424/497 |
| 4,404,183 | 9/1983 | Kawata et al. | 424/19 |
| 4,412,986 | 11/1983 | Kawata et al. | 424/80 |
| 4,673,564 | 6/1987 | Kawata et al. | 424/494 |
| 4,983,609 | 1/1991 | Fujii | 514/274 |
| 5,126,145 | 6/1992 | Evanstad et al. | 424/495 |

FOREIGN PATENT DOCUMENTS

| | | |
|---|---|---|
| 58-99411 | 6/1983 | Japan. |
| 58-109411 | 6/1983 | Japan. |
| 63-115817 | 5/1988 | Japan. |
| 2-49720 | 2/1990 | Japan. |
| 1430684 | 3/1976 | United Kingdom. |
| 2192880 | 3/1987 | United Kingdom. |

*Primary Examiner*—Edward Webman
*Attorney, Agent, or Firm*—Armstrong, Westerman, Hattori, McLeland & Naughton

[57] ABSTRACT

The solid preparation of the invention is prepared by dissolving 3-[3-(6-Benzoyloxy-3-cyano-2-pyridyloxycarbonyl)benzoyl]-1-ethoxymethyl-5-fluorouracil (hereinafter referred to as "BOF-A2") and a water-soluble polymer in a organic solvent completely, followed by forming preparation of amorphous powder prepared by removing the organic solvent.

The solid preparation is useful to enhance solubility of BOF-A2 and to accomplish rapid absorption of BOF-A2 through the alimentary canal.

5 Claims, No Drawings

PARTICULATE PREPARATION CONTAINING A FLOURRACIL DERIVATIVE AND HYDROXYPROPYLMETHYL-CELLULOSE

FIELD OF THE INVENTION

The invention relates to a solid preparation.

DISCLOSURE OF THE INVENTION

It is known that 3-[3-(6-Benzoyloxy-3-cyano-2-pyridyloxycarbonyl)benzoyl]-1-ethoxymethyl-5-fluorouracil (hereinafter referred to as "BOF-A2") is converted, after administration in vivo, into 1-ethoxymethyl-5-fluorouracil (hereinafter referred to as "EM-FU") and 3-cyano-2,6-dihydropyridine (hereinafter referred to as "CNDP") by chemical hydrolysis and enzymolysis, EM-FU being gradually converted into 5-fluorouracil, CNDP working as a metabolic inhibitor and showing continuous and strong anti-cancer activity.

Because of the slight solubility of BOF-A2 in water, rapid absorption of BOF-A2 from the alimentary canal can not be expected.

In general, as means to enhance elution of an active ingredient with slight solubility, exemplified are (1) converting the active ingredient into a soluble derivative and using the derivative, (2) adding a solubilizer, such as surface active agents and the like in preparing the preparation. However, these means do not produce a satisfactory result in the case of BOF-A2. More specifically, in the case of BOF-A2, BOF-A2 has a relatively high molecular weight and is easily hydrolyzed so that it is extremely difficult to improve the solubility of BOF-A2 by introducing hydrophilic groups. Further, in preparation containing added surface active agents, such as polysorbate 80, sodium lauryl sulfate, stearic acid polyoxyl 40 and the like generally used as a solubilizer, the elution improvement effect of the solubilyzer is small and impractical.

The inventors conducted research to improve the solubility of BOF-A2 conditions and accomplished the present invention.

Thus, the present invention relates to a solid preparation characterized in that dissolving BOF-A2 and a water-soluble polymer in an organic solvent completely and preparing a preparation of amorphous powder obtained by removing the organic solvent.

As the water-soluble polymer used in the invention, previously known polymers can be widely used, for example, hydroxypropylmethylcellulose, hydroxypropylcellulose, polyvinylpyrrolidone, methacrylic acid copolymer and the like can be exemplified. In the polymers, hydroxypropylmethylcellulose and hydroxypropylcellulose are preferable in view of absorbability, hydroxypropylmethylcellulose is particularly preferable in view of preservation stability.

The hydroxypropylmethylcellulose used in the invention has 19 to 30% of methoxy groups and 4 to 12% of hydroxypropyl groups, and a viscosity of 3 to 30000 cps (2% water solution, 20° C.) preferably 3 to 4000 cps.

In the invention, as the organic solvent, all of known solvents can be used as long as they are capable of dissolving a water-soluble polymer completely, more specifically lower alcohols, such as methanol, ethanol, isopropanol and the like, ketones, such as acetone, methylethylketone and the like, halogenated hydrocarbon(s), such as dichloromethane, dichloroethane, chloroform, carbon tetrachloride and the like or a mixture thereof can be exemplified. Further, purified water can be added into these solvents, if necessary. Of the organic solvents, lower alcohols and halogenated hydrocarbon(s) are preferable in view of solubility and subsequent removal, a mixed solvent of dichloromethane with methanol or ethanol is particularly preferable.

When producing the solid preparation of the invention, first of all, BOF-A2 and a water-soluble polymer are completely dissolved in the above organic solvent. Although the mixing proportion of BOF-A2 and a water-soluble polymer is not limited, the former is normally used at least 0.01 times as much as the amount of the latter by weight, preferably about 0.05 to about 3 times, in particular, preferably about 0.05 to about 1 times. When the mixing proportion of the water-soluble polymer to BOF-A2 is too low, the mixture are not likely to become amorphous, when the mixing proportion is too high, the stability of BOF-A2 become worse.

In the present invention, amorphous powder is then obtained by removing the organic solvent. As means to remove an organic solvent, known processes can be widely used without being limited, for example a method using evaporator, a method of freeze-drying, a method of spray-drying and the like are exemplified. In the methods, a method of spray-drying is especially preferable. The amorphous powder thus obtained is used to prepare various solid preparation by using a usual method of preparing solid preparations. More specifically, solid preparations for oral administration, such as powder, fine granule, granule, capsule, tablet and the like can be prepared by a usual method to prepare the preparation after adding further excipient, disintegrator, binder, lubricant and the like to the amorphous powder.

EXAMPLES

The examples and comparative examples are further illustrative of the present invention.

EXAMPLE 1

A powder was prepared by dissolving 4 g of BOF-A2 and 0.04 g of hydroxypropylmethylcellulose in a mixed solvent of 19 g of acetone and 75 g of dichloromethane, followed by spray-drying the solution. Powder medicine was obtained by adding 7.8 g of lactose to 2.2 g of the spray-dried powder obtained and admixing the mixture.

EXAMPLE 2

A powder was prepared by dissolving 4 g of BOF-A2 and 0.4 g of hydroxypropylmethylcellulose in a mixed solvent of 19 g of methanol and 75 g of dichloromethane, followed by spray-drying the solution. Powder medicine was obtained by adding 7.8 g of lactose to 2.2 g of the spray-dried powder obtained and admixing the mixture.

EXAMPLE 3

A powder was prepared by dissolving 4 g of BOF-A2 and 4 g of hydroxypropylmethylcellulose in a mixed solvent of 19 g of methanol and 75 g of dichloromethane, followed by spray-drying the solution. Powder medicine was obtained by adding 6 g of lactose to 4 g of the spray-dried powder obtained and admixing the mixture.

EXAMPLE 4

A powder was prepared by dissolving 2 g of BOF-A2 and 4 g of hydroxypropylmethylcellulose in a mixed solvent of 19 g of methanol and 75 g of dichloromethane, followed by spray-drying the solution. Powder medicine was obtained by adding 2 g of lactose to 3 g of the spray-dried powder obtained and admixing the mixture.

EXAMPLE 5

A powder was prepared by dissolving 2 g of BOF-A2 and 6 g of hydroxypropylmethylcellulose in a mixed solvent of 19 g of ethanol and 75 g of dichloromethane, followed by spray-drying the solution. Powder medicine was obtained by adding 2 g of lactose to 3 g of the spray-dried powder obtained and admixing the mixture.

EXAMPLE 6

A powder was prepared by dissolving 2 g of BOF-A2 and 4 g of hydroxypropylcellulose in a mixed solvent of 19 g of methanol and 75 g of dichloromethane, followed by spray-drying the solution. Powder medicine was obtained by adding 2 g of lactose to 3 g of the spray-dried powder obtained and admixing the mixture.

EXAMPLE 7

A powder was prepared by dissolving 2 g of BOF-A2 and 4 g of polyvinylpyrrolidone in a mixed solvent of 19 g of methanol and 75 g of dichloromethane, followed by spray-drying the solution. Powder medicine was obtained by adding 2 g of lactose to 3 g of the spray-dried powder obtained and admixing the mixture.

COMPARATIVE EXAMPLE 1

A fine powder having about 5 μm in diameter of average particle was prepared by grinding 20 g of original BOF-A2 with an air-flow pulverizer. Powder medicine was obtained by adding 2 g of lactose to 3 g of the fine powder obtained and admixing the mixture.

EXAMPLE 8

A powder was prepared by dissolving 300 g of BOF-A2 and 15 g of hydroxypropylmethylcellulose in a mixed solvent of 270 g of ethanol and 2415 g of dichloromethane, followed by spray-drying the solution.

| spray-dried powder | 105 g |
| lactose | 59 g |
| crystalline cellulose | 27 g |
| anhydrous silicic acid | 2 g |
| hydroxypropylmethylcellulose | 7 g |
| total | 200 g |

50% of fine granule was obtained by mixing spray-dried powder, lactose and crystalline cellulose and conducting flow granulation using 4% of hydroxypropylmethylcellulose water solution as a binder solution, followed by adding anhydrous silicic acid and mixing the mixture.

EXAMPLE 9

| spray-dried powder obtained in example 4 | 105 g |
| lactose | 22 g |
| cornstarch | 15 g |
| anhydrous silicic acid | 1 g |
| hydroxypropylmethylcellulose | 7 g |
| total | 150 g |

100 mg of capsule of BOF-A2 was obtained by mixing spray-dried powder, cornstarch and light anhydrous silicic acid, adding lactose into the mixture and conducting flow granulation using 4% of hydroxypropylmethylcellulose water solution as a binder solution, followed by adding anhydrous silicic acid and mixing the mixture to give powder for capsule, and filling up the powder in a gelatine capsule.

EXAMPLE 10

A powder was prepared by dissolving 200 g of BOF-A2 and 20 g of hydroxypropylmethylcellulose in a mixed solvent of 180 g of ethanol and 1610 g of dichloromethane, followed by spray-drying the solution.

| spray-dried powder | 110 g |
| lactose | 22.5 g |
| crystalline cellulose | 10 g |
| Croscarmellos Sodium | 5.3 g |
| anhydrous silicic acid | 1.5 g |
| magnesium stearate | 0.7 g |
| total | 200 g |

100 mg of tablet of BOF-A2 was obtained by mixing spray-dried powder, lactose, crystalline cellulose and anhydrous silicic acid and further adding magnesium stearate, followed by directly compressing the mixture.

EXAMPLE 11

A powder was prepared by dissolving 200 g of BOF-A2 and 20 g of hydroxypropylmethylcellulose in a mixed solvent of 180 g of ethanol and 1610 g of dichloromethane, followed by spray-drying the solution.

| spray-dried powder | 110 g |
| hydroxypropylmethylcellulose | 8 g |
| anhydrous silicic acid | 3 g |
| magnesium stearate | 1 g |
| total | 122 g |

A capsule was obtained by mixing this powder and anhydrous silicic acid and conducting flow granulation using 4% of hydroxypropylmethylcellulose water solution as a binder solution, followed by adding magnesium stearate, admixing the mixture and filling up 122 mg of the resulting powder in one capsule.

COMPARATIVE EXAMPLE 2

| micronized powder (average particle diameter: about 5 μm) | 100 g |
| lactose | 64 g |
| crystalline cellulose | 28 g |
| hydroxypropylmethylcellulose | 8 g |
| total | 200 g |

50% of fine granule was obtained by mixing micronized original powder, lactose and crystalline cellulose, followed by conducting flow granulation using 4% of hydroxypropylmethylcellulose water solution as a binder solution.

TEST EXAMPLE 1 (SOLUBILITY TEST)

An amount corresponding to 100 mg of BOF-A2 of each sample obtained in examples 2 to 4, example 6, example 7 and comparative example 1 was weighed precisely respectively, each sample being put into a dissolution test solution, the dissolution rates of BOF-A2 after 5 minutes, 10 minutes, 20 minutes, 30 minutes, 40 minutes, 50 minutes and 60 minutes was determined with automatic dissolution test apparatus (product of JASCO DT-610). As the dissolution test solution, used was 500 ml of the solution prepared by adding 0.5% of hydroxypropylmethylcellulose and 1.5% of polyoxyethylenecetylether in purified water. The determination of dissolution rate of the BOF-A2 was conducted by using a standard solution prepared by dissolving 2100 mg of BOF-A2 in 500 ml of acetonitrile and determining the difference of absorbance between standard solution and sample solutions at 266 nm and 360 nm in wave length. The results were shown in table 1.

TABLE 1

| Powder | Time (min) | | | | | | | |
|---|---|---|---|---|---|---|---|---|
| | 5 | 10 | 15 | 20 | 30 | 40 | 50 | 60 |
| Example 2 | 37.9 | 49.6 | 55.8 | 59.9 | 64.7 | 67.1 | 68.9 | 70.3 |
| Example 3 | 39.3 | 52.2 | 58.3 | 62.7 | 68.2 | 71.5 | 74.6 | 76.8 |
| Example 4 | 45.1 | 56.4 | 63.4 | 68.5 | 75.9 | 80.6 | 84.1 | 86.8 |
| Example 6 | 20.8 | 42.0 | 56.1 | 67.1 | 78.1 | 83.6 | 87.3 | 89.8 |
| Example 7 | 23.4 | 32.6 | 39.6 | 45.3 | 55.0 | 62.8 | 68.7 | 73.3 |
| Comparative Example 1 | 0.2 | 0.2 | 0.3 | 0.3 | 0.4 | 0.4 | 0.4 | 0.5 |

TEST EXAMPLE 2 (ABSORPTION TEST USING BEAGLE)

Using 3 or 4 beagles weighing about 10 kg, each preparation prepared in examples 8 to 11 and comparative example 2 was orally administered in an amount corresponding to 100 mg of BOF-A2 per beagle respectively, EM-FU concentration in plasma (μg/ml) at 1 to 24 hours after administration being determined, maximum concentration in plasma [Cmax (μg/ml)] concentration in plasma and area under the curve [AUC (μg.hr/ml)] being determined. Non-changed compound, i.e., BOF-A2 was not detected in plasma so that the concentration of metabolite, i.e., EM-FU was used as an index of absorption in all cases. The results were shown in table 2.

TABLE 2

| Sample | Maximum concentration in plasma [Cmax (μg/ml)] | Concentration in plasma and area under [AUC (μg · hr/ml)] |
|---|---|---|
| Example 8 | 4.0 | 141 |
| Example 9 | 3.9 | 152 |
| Example 10 | 3.2 | 130 |
| Comparative | 0.05 | 0.9 |

We claim:

1. A solid preparation of 3-[3-(6-benzoyloxy-3-cyano-2-pyridyloxycarbonyl)-benzoyl]-1-ethoxymethyl-5-fluorouracil having enhanced water solubility consisting essentially of 3-[3-(6-benzoyloxy-3-cyano-2-pyridyloxycarbonyl)-benzoyl]-1-ethoxymethyl-5-fluorouracil and about 0.05 to 3 parts by weight of hydroxypropylmethylcellulose per part of the 3-[3-(6-benzoyloxy-3-cyano-2-pyridyloxycarbonyl)-benzoyl]-1-ethoxymethyl-5-fluorouracil, said solid preparation being prepared by dissolving the 3-[3-(6-benzoyloxy-3-cyano-2-pyridyloxycarbonyl)benzoyl]-1-ethoxymethyl-5-fluorouracil and hydroxypropylmethylcellulose in an organic solvent, and then removing the organic solvent to form an amorphous powder.

2. The solid preparation as defined in claim 1, which contains about 0.05 to 1 part by weight of hydroxypropylmethylcellulose per part of 3-[3-(6-benzoyloxy-3-cyano-2-pyridyloxycarbonyl)benzoyl]-1-ethoxymethyl-5-fluorouracil.

3. The solid preparation as defined in claim 1, wherein said organic solvent is a mixed solvent of methylene chloride and methanol, ethanol or isopropanol.

4. The solid preparation as defined in claim 3, wherein said organic solvent is a mixed organic solvent of methylene chloride and methanol or ethanol.

5. The solid preparation as defined in claim 1, wherein the organic solvent is removed by spray-drying.

* * * * *